United States Patent [19]

Iiams

[11] Patent Number: 5,320,161
[45] Date of Patent: Jun. 14, 1994

[54] GELLED FORMALDEHYDE TRANSPORT METHOD

[75] Inventor: Bruce A. Iiams, Anchorage, Ak.

[73] Assignee: Atlantic Richfield Company, Los Angeles, Calif.

[21] Appl. No.: 929,983

[22] Filed: Aug. 14, 1992

[51] Int. Cl.$^5$ ............................. F28D 1/00; F28D 5/00
[52] U.S. Cl. ............................................. 165/2; 165/1; 165/41; 165/132; 126/343.5 A; 137/340; 62/268
[58] Field of Search ................... 165/41, 132, 1, 2; 126/343.5 A, 343.5 R; 137/340; 62/268

[56] References Cited

U.S. PATENT DOCUMENTS

| 4,230,138 | 10/1980 | Tanaka | 165/132 |
| 4,415,018 | 11/1983 | Rosenberger | 165/41 |
| 4,441,887 | 4/1984 | Funk | 44/51 |
| 4,470,402 | 9/1984 | Tanaka | 165/132 |
| 4,603,733 | 8/1986 | Loevinger | 165/132 |

OTHER PUBLICATIONS

"Formaldehyde" by J. F. Walker, 3rd Edition, Reinhold Publishing Corp., New York, 1964, pp. 98–105.
Kirk-Othmer "Encyclopedia of Chemical Technology", John Wiley & Sons, Inc., New York, vol. 10, pp. 77–81, vol. 18, pp. 78–79 (no date), vol. 23, pp. 376–379 & 388–392 (1983).

Primary Examiner—John K. Ford
Attorney, Agent, or Firm—Michael E. Martin

[57] ABSTRACT

Formaldehyde and similar biocides are transported in a gelled, semi-solid or solid state by providing formaldehyde in a concentration in methanol of about fifty-five percent (55%) to eighty-five percent (85%) by weight, loading the solution in rail cars or truck transport tanks in a liquid state and cooling the solution to a gelled, semi-solid or solid state for transport to a destination followed by reheating the solution and/or mixing with a solvent for discharge to an application such as the produced water flowstreams from Alaskan North Slope oil fields, for example.

11 Claims, 1 Drawing Sheet

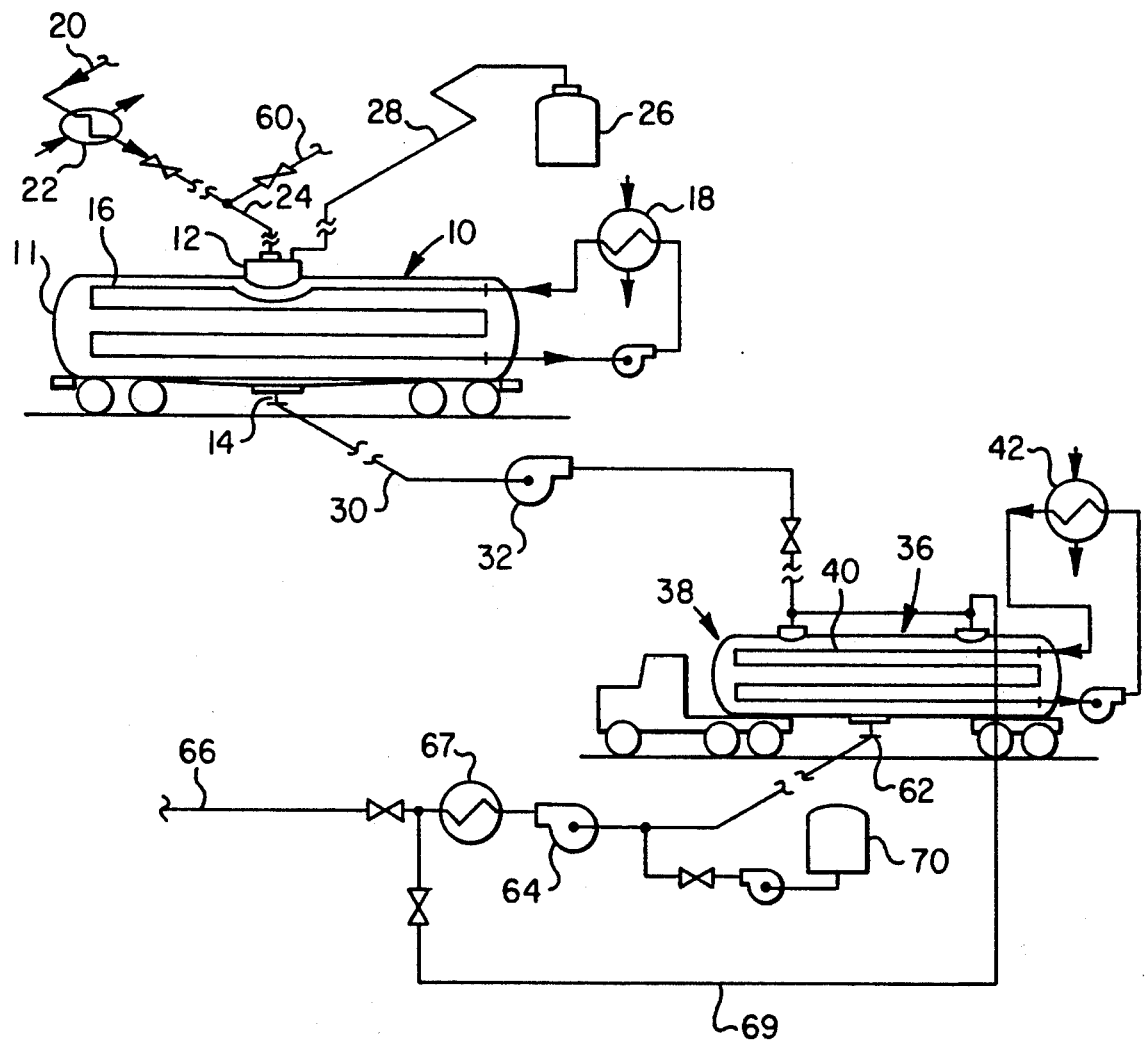

GELLED FORMALDEHYDE TRANSPORT METHOD

BACKGROUND OF THE INVENTION

1. Field of the Invention

The present invention pertains to a method for transporting relatively large quantities of formaldehyde as a methanol-formaldehyde mixture, which may contain water, and which is maintained in a gelled, semi-solid or solid form during transport.

2. Background Art

Aqueous and methanol solutions of formaldehyde are used in relatively large quantities as a biocide for treating water in certain oil and gas production operations. For example, in the production of oil and gas from the Alaskan North Slope oil fields, large quantities of formaldehyde are mixed with the waters which are both injected in and produced from the oil-bearing formations to minimize certain organic activity. Formaldehyde and similar biocides are being considered for use in these applications in similar operations in other parts of the world. The remote location of the treatment facilities where the formaldehyde is injected into the water requires transport of this chemical to its point of injection by both rail and motor truck forms of transportation.

Formaldehyde-methanol-water mixtures are known to form complex mixtures of methylene glycol, methanol-formaldehyde hemiacetal, and their analogous oligimers and polymers as well as small amounts of the three original components. Commercial solutions usually contain minor impurities such as formate, aldol condensates, dimethyl ether, trace corrosion products and other process contaminants. Also additives to inhibit formation and retard precipitation of formaldehyde polymers, are usually present. Formaldehyde solutions are "stabilized" to withstand minimum temperatures and exposure times to eliminate or minimize precipitation of solid phase material. Commercial formaldehyde solutions are stabilized by temperature control, alcohols, dilution, minimized catalytic polymer forming impurities and various additives well known to those skilled in the art. Liquid products marketed for their formaldehyde content are generally solutions containing water, methanol and/or butanol.

Conventional formaldehyde solution transport and storage technology uses solutions dissolved at high temperatures and subsequent formaldehyde polymer precipitation inhibited by methanol, dilution and inhibitory additives well known to the art. These measures slow the precipitation of formaldehyde polymers at moderate temperatures for only a relative short time, usually several months at the manufacturers' minimum recommended temperatures and days or weeks at the conditions on the North Slope of Alaska.

Moreover, it is known that both aqueous and alcoholic solutions of formaldehyde, as used widely in various industrial processes, have upper limits of concentration of the formaldehyde in the solvent to retard precipitation at normal ambient temperatures. Such precipitation is, of course, unwanted in most applications of formaldehyde solutions. On the other hand, the substantial amount of transport required to place large quantities of formaldehyde in the afore-mentioned region for its intended use has raised certain concerns regarding avoidance of uncontained spills during transport and storage. Modification of the product and its method of transport to prevent spillage by gelling the formaldehyde solution will allow the use of transport and storage containers which are larger and are not required to meet overly-strict structural requirements. In other words, the hazards associated with the transport and storage of formaldehyde solutions can be reduced without the additional cost presently associated with transport and handling of this substance. It is to this end that the present invention has been developed with a view to improving certain methods for transporting and storing relatively large quantities of formaldehyde and similar compositions, including their use as biocides.

SUMMARY OF THE INVENTION

The present invention provides a method for transporting and storing formaldehyde solutions in a gelled, semi-solid or solid form to minimize uncontained spillage, minimize shipping volumes and extend product quality and product life.

The invention embraces the gellation and solidification properties of the methanolic formaldehyde solutions at any low temperature up to ambient temperatures to more reliably, safely and economically transport concentrated formaldehyde solutions.

The concentrated methanolic formaldehyde solutions used herein include the thermal control as primarily a cooled system (recommended storage temperatures, typically from below 0 F., up to about 90 F.) as a beneficial part of the processing, transportation and application with heating as a transient condition to be used for storage or specific operations whereas commercial formaldehyde solutions and their handling emphasize warmed systems (minimum recommended temperatures, typically 40–140 F.) with cooling as a transient condition to be minimized for storage times 3 to 12+ months.

In accordance with one important aspect of the present invention, formaldehyde solutions are provided which will gel or form a semi-solid or solid substance as a function of temperature to facilitate transportation from a point of manufacture to a point of use such as the Alaskan North Slope oil fields. Substantially conventional transport vehicles such as rail tank cars and motor truck tankers with insulated or uninsulated tanks, as needed, and with heat transfer means for warming or cooling the tank cargo are used to transport a concentrated aqueous or alcohol solution of formaldehyde in a gelled, semi-solid or solid form to minimize contamination in the event of an unwanted spill or discharge.

In accordance with another important aspect of the present invention, formaldehyde and similar biocide solutions are provided which include about fifty-five percent (55%) to eighty-five percent (85%) formaldehyde by weight and zero percent (0%) to fifteen percent (15%) water by weight and the remainder being an excess of methanol over water in the solution. The properties of the basic formaldehyde-methanol-water mixture may be modified by substituting other alcohols, including diols and triols, for a portion of the methanol. In all cases the total alcohol weight fraction exceeds the water weight fraction. Numerous additives, side products and contaminants used or existing at low concentrations in formaldehyde solutions, known to those skilled in the art, are also included in the scope of this invention, their sum being less than 1% w/w.

In accordance with still another aspect of the present invention, there is provided a method for transporting formaldehyde wherein a particular formaldehyde composition may be partially cooled prior to loading into a rail tank car and the like and then further cooled to form a gelled solid by utilizing ambient, evaporative, chilled glycol or other cooling processes. At the point of discharge of the formaldehyde solution from the rail tank car, the cargo is heated to provide an extrudable solid, a liquified slush or viscous liquid, and sheared with a pump or displaced with pressure gas to a motor truck tank or a storage tank. The rail car and motor truck cargo may be cooled to congeal or gel the formaldehyde by circulation of a heat transfer fluid through a heat transfer jacket or coil arrangement associated with the tank or whereby the tank is allowed to remain parked until ambient cooling of the solution permits transport in the gelled state. The method of the present invention further contemplates the unloading of the tank of the truck or rail car by circulation of a heated fluid through a jacket or heat transfer coil arrangement associated with the tank and then direct use of full strength formaldehyde or dilution of the formaldehyde to meet regulatory and other usage requirements prior to use.

The present invention provides certain advantages heretofore unrealized in handling and using formaldehyde and similar biocide materials in the above-mentioned type of operations. Such advantages include reduced transportation costs due to shipping a higher concentration of the formaldehyde, minimization of uncontained spill risk, the use of existing types of shipping containers and the elimination of specialized high-strength containers or extension of the utility of such containers by reducing the per unit volume shipping costs of useful formaldehyde, minimal retrofitting of existing transport and storage facilities and the use of current transportation systems. These advantages, together with other superior features and important aspects of the present invention, will be further recognized by those skilled in the art upon reading the detailed description which follows in conjunction with the drawing.

BRIEF DESCRIPTION OF THE DRAWING

The drawing figure illustrates in somewhat diagrammatic form certain elements used in the transport and storage method of the present invention.

DESCRIPTION OF PREFERRED EMBODIMENTS

Relatively few biocides, including formaldehyde, acrolein, glutaraldehyde and some of their derivatives and related compositions, have been determined to have significant antimicrobial activity when injected into produced water flowstreams such as are handled in oil and gas production from the Alaskan North Slope. The level of production activity in these fields has required monthly volumes of more than 300,000 gallons of formaldehyde solutions having a concentration of about thirty-seven percent (37%). Mixing this biocide with produced water scavenges hydrogen sulfide, reduces corrosion tendencies in the piping and pressure vessels of the system, both chemically and biologically benefits oil-water separation and reduces biomass in the produced water. Such usage produces collateral benefits such as reduced hazardous waste generation (iron sulfides, for example) and improved injectivity of the treated water when used as a stimulant to produce additional oil from the reservoir. The shipping and handling of this dilute biocide to the North Slope of Alaska results in high transportation costs and certain spill risks. Currently the spill risks are minimized by the use of high-strength containers that have only about 5,000 gallons capacity.

The present invention contemplates alleviating some of the costs and risks associated with the use of formaldehyde and similar bactericides in the above-mentioned application. The present invention contemplates the use of a formaldehyde composition having about fifty-five percent (55%) to eighty-five percent (85%) formaldehyde by weight of the total composition, zero (0) to fifteen (15) percent water by weight of the total composition and the remainder of the composition being methanol provided that the methanol concentration always exceeds the water content. More particularly, the present invention contemplates the use of a formaldehyde composition having about sixty-two percent (62%) to seventy-four percent (74%) formaldehyde, by weight of the total composition and a total water content of from one percent (1%) to eight percent (8%), by weight, the remainder being methanol. One embodiment is a methanolic solution with about 6.63 pounds per gallon formaldehyde content (about seventy-two percent (72%)) and containing 0.01 to ten (10) ppm of a tracer dye, such as fluorescein.

The gellation properties of this solution could be adjusted for summer and winter climatic conditions at the point of manufacture by changing the water content (and implicitly, the paraformaldehyde content also) between approximately 1.0 to 3.0 percent water and 0.5 to 1.5 percent water, respectively. The inclusion of a tracer dye is advantageous for early detection of leakage, and also allowing easy visual differentiation of any melted gel and unmixed water/methanol stocks.

Still further, the present invention contemplates that a concentration of formaldehyde in the total composition in the range of 6.50 pounds per gallon to 6.74 pounds per gallon would further simplify field handling by allowing the thawed/softened/melted gel to be blended at a one to one ratio with water to yield the thirty-seven percent (37%) formaldehyde composition used and presently registered with authorities as a bactericide. The above-mentioned concentrations of formaldehyde result in a gelled, semi-solid or solid material at ambient temperatures normally found north of latitude sixty degrees (60°) north, particularly in substantially the entire State of Alaska, U.S.A.

Still further, the present invention contemplates that the undiluted material, melted or solid, may be applied directly into the point of use if appropriate. In the North Slope oilfield systems, direct injection as a liquid is usually preferable. Bactericidal use of the concentrated formaldehyde requires appropriate registration with federal authorities.

Each manufacturing site should be treated individually depending on processing differences including time, water content, impurities and additives before settling on the final composition specification. Also the application at hand should be evaluated for performance requirements before selecting the final composition specification.

The initial gellation and solidification temperatures and the final liquefaction and clarification temperatures tend to increase with thermal age due to polymer formation and growth until precipitate separation occurs. For the purposes at hand in Alaska, best implementation for a given feedstock keeps intermediate storage and processing times low. This allows the formaldehyde concentration to be kept as high as possible within the constraints of fixed transportation and application systems.

This approach has several inherent advantages over current commercial formaldehyde solutions. In the solidified form, as a solid block, it is safer from accidental release because of its single particle nature, high latent heat of fusion, lower surface to volume ratio. A preliminary observation is that the solidified material is a much less hazardous substance at ambient temperatures. It can be shipped as a solid block through high risk areas but is readily transferable as a liquid after thawing from simple, closed transportation and handling systems. Similarly, the gelled, highly viscous material retains much advantage to prevent spill, spread and vapor emissions.

This invention contemplates that formaldehyde solutions in accordance with the invention would be in a gelled, semi-solid or solid form while undergoing transport by rail or over-land truck transport as well as possibly by marine transport. However, since the solution would be in a gelled, semi-solid or solid state under ambient temperature conditions during such transport, it is necessary to perform heating, cooling and mixing operations at certain stages in the transport and storage of the material. A formaldehyde solution which would become a gelled semi-solid material while being transported by rail car in an uninsulated or lightly insulated tank may require cooling at or after loading into the tank and then heating of the material prior to unloading to facilitate flow. The same processes may be required to be carried out when loading and unloading the material with respect to a tank truck-type transport vehicle. Still further, when the product has reached its final destination and is stored preparatory to its intended use, it may then be returned to a liquid state by mixing with a predetermined amount of water, for example, to bring the formaldehyde concentration to the required amount and also to facilitate flow of the material. For example, at the place of manufacture, considering the geographical location of existing manufacturing facilities, a methanolic formaldehyde composition having a formaldehyde content of about seventy-two percent (72%) would likely require partial cooling during loading into a rail tank car type transport vehicle to produce a cloudy, white, highly viscous liquid. Upon loading of the viscous liquid into the rail car, additional ambient cooling, evaporative cooling or other means of cooling the solution may be carried out to minimize any delay in commencing the journey to the point of use. Evaporative cooling is advantageous because of its high rate of heat transfer, the ease of loading the material while still in a liquid state and the resultant change in the composition of the material to a higher concentration of the formaldehyde as a result of evaporation of the solvent such as water or methanol. On evaporative cooling, whether vacuum or inert gas swept, good engineering practices are required.

Alternatively, or in combination with the preceeding cooling method, slow loading (1-2 weeks fill and chill time) of a tank may be desirable for reduced capital outlay and efficient energy use. A continuously utilized chiller minimizes capital outlay and maximizes portability. Further, by slower loading, less extreme coolant temperatures are required to chill the product. "Higher" chilling temperatures allow greater energy efficiency to be realized at lower capital cost.

The drawing figure is composite diagram showing the major components and systems which would be required to transport the formaldehyde composition from its point of manufacture to its final destination for placement in a suitable storage facility preparatory to its end use. The drawing figure illustrates a railroad tank car 10 having a conventional cargo tank 11 provided with an expansion and loading dome 12 and a center, bottom discharge conduit 14. The tank car 10 is modified to include a heat exchange coil arrangement, generally designated by the numeral 16, which may comprise a jacket around the cargo tank or may comprise a serpentine conduit or manifold mounted on the inner or outer surface of the tank 11. A suitable heat exchange fluid is circulated through the heat exchange coil arrangement 16 and through a heat exchanger 18. The heat exchanger 18 may comprise a conventional steam boiler whereby steam is supplied to the coil arrangement 16 and condensed steam is recirculated to the heat exchanger 18. Other types of heat exchange fluids, such as glycols, may be preferable and can be utilized to either heat or cool the contents of the tank 11 by circulation through the coil arrangement 16.

A source of formaldehyde in methanol solution in the preferred concentration range described above may be connected to a tank loading conduit 20 and, if necessary, either heated or cooled by circulating the formaldehyde solution through a heat exchanger 22. The heated or cooled formaldehyde solution is then loaded into the tank 11 by way of a suitable loading conduit 24. If evaporative cooling of the formaldehyde solution within the tank 11 is relied on, vapor collected in the tank 11 may be conducted to a suitable vapor recovery unit 26 by way of a conduit 28.

When the tank car 10 is suitably loaded with the prescribed formaldehyde solution, transport of the car to an intermodal transfer point may be carried out or transport to the final destination may also, of course, be carried out. The tank 11 is preferably provided with sufficient insulation to reduce daily temperature fluctuations on the inner surface of the tank so that, particularly on sunny days, minimal heating of the contents of the tank will occur. If the tank car 10 is transported to Alaska from a point of origin south of the 60th Parallel with formaldehyde in the above-mentioned concentration, a substantially gelled, semi-solid or solid mass will exist within the tank 11 with the exception of minor amounts of liquid in methanolic inclusions and, perhaps, minor amounts of formaldehyde hemiacetals and glycols. In all events, the majority of the concentrated formaldehyde solution in the tank 11 will be semi-solid, particularly once the cargo reaches Anchorage, Alaska and is shipped on to the railhead at Fairbanks, Alaska. The heat exchanger 18 may remain on board the tank car 10 and be used to heat or cool the contents of the tank 11 as required during transit and at the car unloading facility. Alternatively, of course, suitable heat exchangers or heating fluid may be supplied to the heat exchange coil arrangement 16 at the unloading facility from a stationary source of such fluid. Depending on ambient temperatures, the contents of tank 11 may be allowed to "thaw" at ambient conditions after passing through areas where spills might be a greater risk.

The present invention further contemplates that the rail car 10, as well as other tanks to be loaded with the above-mentioned formaldehyde solution, may be filled with solution at a temperature near the pour point and the depth of the solution in the tank at temperature conditions above the pour point do not allow much fall and separation before gelation and solidification. For example, a 20,000 gallon capacity rail car may be loaded at the rate of about 40 to 200 liters per minute, whereby the depth of the product increases then at a rate of about 2 to 10 millimeters per minute. This loading condition will, with suitable cooling, restrict separated polymer to less than about two millimeters depth before gelation occurs. The composition of the formaldehyde solution used in carrying out the present invention also contemplates a flashpoint temperature for the solution to be in the range of at least 72° F. to 100° F. regardless of the pour point temperature.

When the rail car 10 reaches its destination (for example, Fairbanks, Alaska) and the cargo is transferred to another mode of transportation or placed in storage, the heat exchanger 18 is supplied with a suitable source of heat to circulate a fluid through the heat exchange coil arrangement 16 to warm the contents of the tank 11 to a temperature which will allow free flow of the formaldehyde solution through the center discharge conduit 14 to a conduit 30 which is connected to a suitable pump 32. The pump 32 may further process the solution by shearing to remix the solution and condition it for ease of pumping to a transport tank 36 of a conventional over-the-road tractor-trailer unit 38. The tank 36 is also provided with suitable heat exchange conduit arrangement 40 which may comprise a jacket around the tank 36 or a suitable serpentine conduit, either inside or outside of the tank 36, and connected to a suitable heat exchanger 42 for providing a source of heat or cooling as the case may require to adjust the temperature of the solution inside the tank.

The tank 36 may be insulated or uninsulated, depending on its operating environment and hazard minimization requirements. Depending on the time of year, particularly north of the 60th Parallel, the formaldehyde solution in the tank 36 may be allowed to solidify by merely parking the trailer of the unit 38 for a predetermined period of time until the solution gels or solidifies.

During unloading of the tank car 10, if the formaldehyde solution is not increased to a temperature which would cause free, relatively unrestricted flow to the pump 32, nitrogen gas or the like may be introduced into the tank interior through a suitable conduit 60 to force a more rapid rate of discharge, taking into consideration pressure limits of the tank 11, of course.

When the tractor-trailer unit 38 reaches its destination, such as the North Slope oil fields, heated fluid is circulated through the heat exchange conduit arrangement 40 to warm the formaldehyde solution in the tank 36 for discharge from a conventional center bottom discharge conduit 62. The formaldehyde solution may be circulated by a pump 64 directly to an application conduit 66 by way of a heat exchanger 67. Unloading of the tank 36 may be enhanced by recirculating thawed solution back to the tank via a conduit 69. Methanol and/or water may be added to the solution in the application conduit 66 and methanol may be added from a tank 70 for freeze protection, cleaning of the system and to increase gel solvency.

The formaldehyde solution concentrations considered to be suitable in accordance with the method of the present invention may increase the formaldehyde content in the solution which may cause precipitates to form, particularly if the water content of the composition is very high. However, the formation of paraformaldehydes, hemiacetal oligimers and polymer analogs in the gelled, semi-solid or solid state of the composition is not considered undesirable as long as substantial separation of the gel from the solid form is not detrimental to loading and unloading the material or does not substantially reduce the available formaldehyde monomers content upon application of the composition to its intended use. The above-mentioned loading processes contemplate minimal separation of the solution into separate liquid, gel and solid forms.

The rate of thermal aging, initial gellation and solidification temperatures and the final melting range, flash point at various stages and other properties are design matters for compositional selection within the scope of this invention and the feedstocks available. The chilled thermal mass and total latent heat, temperature history, heat flux and time (integrated heat gain), geographical and seasonal temperature variations, desired application temperature, and equipment limits are some of the variables that should be considered in the specific selection of a methanolic formaldehyde composition for a specific application.

For a given formaldehyde concentrate feedstream, the manufacture of a methanolic formaldehyde composition of lower concentration with methanol addition as is believed to be within the purview of those skilled in the art. Reductions in water content below the current 2–8% and 9–11% water present in paraformaldehyde and 55% methanolic solutions, respectively, are matters of careful operation or enhancement of the current manufacturing processes. An anhydrous formaldehyde feedstream for combination with methanol is possible but the only existing facility is dedicated and has practical economic challenges.

Although preferred embodiments of the present invention have been described herein, those skilled in the art will recognize that various substitutions and modifications may be made to the method without departing from the scope and spirit of the appended claims.

What is claimed is:

1. A method for transporting formaldehyde and like biocide compositions to minimize uncontained spills from transport vehicles, comprising the steps of:
   providing a formaldehyde composition containing approximately fifty-five percent (55%) to eighty-five percent (85%) formaldehyde by weight in a solution containing a solvent of zero percent (0%) to fifteen percent (15%) by weight of water and the remainder methanol and wherein the methanol content is greater than the water content of said composition;
   controlling the temperature of said solution to permit loading said solution into a tank of a first vehicle and loading said solution into said tank of said first vehicle;
   cooling the loaded solution to a temperature which forms at least one of a gel, semi-solid and solid form of said solution;
   transporting said solution in said vehicle to a discharge point; and
   heating said solution to a temperature which will permit flowable discharge of said solution from said tank.

2. The method set forth in claim 1, including the step of:
   transferring said solution to a second vehicle having a solution storage tank thereon;

cooling said solution to a condition which will form at least one of a gel, semi-solid and solid of said solution; and transporting said vehicle to a destination for unloading said solution.

3. The method set forth in claims 1 or 2, including the step of:

mixing said solution with water at said destination to form a liquid formaldehyde solution which is pumpable to mix with water which is to be reduced of bacteria in the presence of said formaldehyde.

4. The method set forth in claim 2, including the step of:

transferring said solution from one of said vehicles to the other of said vehicles by means of a pump capable of shearing said solution.

5. The method set forth in claim 2, including the step of:

discharging said solution from said first vehicle by at least one of pressurized gas and gravity acting on said solution in said tank of said first vehicle.

6. The method set forth in claim 1, including the step of:

cooling said solution in said tank by evaporation of at least one of said solvents.

7. The method set forth in claim 6, including the step of:

recovering said one solvent separate from said solution.

8. The method set forth in claim 1, including the step of:

providing said composition having a concentration of formaldehyde in the range of sixty-two percent (62%) to seventy-four percent (74%) by weight, one percent (1%) to eight percent (8%) water by weight and the balance being substantially methanol.

9. The method set forth in claim 1, including the step of:

providing said solution including a dye for detection of leakage of said solution.

10. The method set forth in claim 3, including the step of:

mixing said solution with water to reduce the concentration of said solution to about thirty-seven percent (37%) by weight.

11. A method for transporting formaldehyde compositions to the Alaskan North Slope to minimize uncontained spills from transport vehicles, comprising the steps of:

providing a formaldehyde composition containing approximately fifty-five percent (55%) to eighty-five percent (85%) formaldehyde by weight in a solution containing a solvent of zero percent (0%) to fifteen percent (15%) by weight of water and the remainder methanol and wherein the methanol content is greater than the water content of said composition;

controlling the temperature of said solution to permit loading said solution as a viscous liquid into a tank of a first vehicle and loading said solution into said tank of said first vehicle;

cooling the loaded solution to a temperature which forms at least one of a gel, semi-solid and solid;

transporting said solution in said first vehicle to a discharge point;

heating said solution to a temperature which will permit flowable discharge of said solution from said tank of said first vehicle;

transferring said solution to a second vehicle having a solution storage tank thereon;

cooling said solution to a condition which will form at least one of a gel, semi-solid and solid of said solution;

transporting said second vehicle to a destination for unloading said solution; and mixing said solution with a solvent at said destination to form a liquid formaldehyde solution which is pumpable to mix with water which is to be reduced of bacteria in the presence of said formaldehyde.

* * * * *